United States Patent
Salah et al.

(10) Patent No.: US 12,370,026 B2
(45) Date of Patent: *Jul. 29, 2025

(54) METHOD OF ENRICHMENT OF A DIGITAL DENTAL MODEL

(71) Applicant: DENTAL MONITORING, Paris (FR)

(72) Inventors: Philippe Salah, Paris (FR); Thomas Pellissard, Clichy (FR); Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/431,128

(22) Filed: Feb. 2, 2024

(65) Prior Publication Data
US 2024/0225797 A1 Jul. 11, 2024

Related U.S. Application Data

(62) Division of application No. 16/965,554, filed as application No. PCT/EP2019/052121 on Jan. 29, 2019, now Pat. No. 11,918,437.

(30) Foreign Application Priority Data

Jan. 30, 2018 (EP) .................................. 18154281

(51) Int. Cl.
*A61C 9/00* (2006.01)
*G06F 18/22* (2023.01)
(Continued)

(52) U.S. Cl.
CPC ............ *A61C 9/0053* (2013.01); *G06F 18/22* (2023.01); *G06T 7/0016* (2013.01); *G06T 7/337* (2017.01);
(Continued)

(58) Field of Classification Search
CPC ..... A61C 9/0053; G06T 7/337; G06T 7/0016; G06T 2201/03; G06T 2207/20084;
(Continued)

(56) References Cited

U.S. PATENT DOCUMENTS 10,460,839 B1 * 10/2019 Ricci ....................... G16H 50/20
11,651,494 B2 * 5/2023 Brown .................... G16H 30/20
382/128

(Continued)

FOREIGN PATENT DOCUMENTS

CA 3147004 A1 * 1/2021 ............. A61C 13/34
CA 2989987 C * 9/2023 ............. A61C 19/05

*Primary Examiner* — Khai M Nguyen
(74) *Attorney, Agent, or Firm* — Ronald M. Kachmarik; Cooper Legal Group LLC

(57) ABSTRACT

Method of enrichment of a reference model to be enriched representing a dental arch. Acquisition, under first real conditions, of a current image of the arch displaying one region. Exploration of the reference model in such a manner as to determine a first view of the reference model, in a first direction of observation the reference image exhibiting a maximum match with the current image. Determination, by comparison of the images, of a first orphan point represented on the current image and not represented on the reference image when the current image is in a first register position in which it is superposed, in the space of the reference model, with the reference image. Addition, in the reference model, of a point on a first straight line parallel to the first direction of observation and passing through the first orphan point in the first register position.

17 Claims, 5 Drawing Sheets

(51) Int. Cl.
  *G06T 7/00*    (2017.01)
  *G06T 7/33*    (2017.01)
  *G16H 30/20*   (2018.01)
  *G16H 30/40*   (2018.01)
  *G16H 50/20*   (2018.01)
  *G16H 50/50*   (2018.01)
  *G16H 50/70*   (2018.01)

(52) U.S. Cl.
  CPC ............. *G16H 30/20* (2018.01); *G16H 30/40* (2018.01); *G16H 50/20* (2018.01); *G16H 50/50* (2018.01); *G16H 50/70* (2018.01); *G06T 2207/20084* (2013.01); *G06T 2207/30036* (2013.01); *G06V 2201/03* (2022.01)

(58) Field of Classification Search
  CPC .......... G06T 2207/30036; G16H 50/50; G16H 50/70; G16H 50/20; G16H 30/20; G16H 30/40; G16F 18/22
  See application file for complete search history.

(56) References Cited

U.S. PATENT DOCUMENTS

| | | | |
|---|---|---|---|
| 11,918,437 B2 * | 3/2024 | Salah | G16H 50/50 |
| 2008/0318179 A1 * | 12/2008 | Liu | A61C 7/00 433/24 |
| 2017/0128164 A1 * | 5/2017 | Bindayel | A61C 7/14 |
| 2017/0128168 A1 * | 5/2017 | Bindayel | A61C 7/14 |
| 2018/0168780 A1 * | 6/2018 | Kopelman | G06V 10/758 |
| 2018/0235437 A1 * | 8/2018 | Ozerov | A61B 5/4552 |

\* cited by examiner

METHOD OF ENRICHMENT OF A DIGITAL DENTAL MODEL

TECHNICAL FIELD

The present invention relates to a method of enrichment of a digital model of a dental arch of a patient, and also to a computer program for the implementation of this method.

PRIOR ART

It is desirable for everyone to get regular check-ups of their dentition, notably in order to verify that the position of their teeth is not undergoing an adverse change. During orthodontic treatment, this adverse change may notably lead to a modification of the treatment. After orthodontic treatment, this adverse change, called "relapse", may lead to the treatment being re-started. Lastly, more generally speaking and independently of any treatment, everyone may wish to track any potential movements of their teeth.

Conventionally, the check-ups are carried out by an orthodontist or a dentist since only they possess the appropriate equipment. These check-ups are therefore costly. Furthermore, the consultations are burdensome.

US 2009/0291417 describes a method allowing three-dimensional models to be created, then three-dimensional models to be modified, notably for the fabrication of orthodontic appliances.

WO 2016 066651 describes a method for monitoring the positioning and/or the shape and/or the aspect of a patient's teeth. This method comprises a step for creating an initial reference model of the teeth, preferably with a 3D scanner, then, at a later time, the creation of a current reference model, by deformation of the initial reference model. This deformation is carried out in such a manner that the current reference model allows views that are as consistent as possible with the images of the teeth acquired at the later time, in particular photos or images from a video taken by the patient themselves.

The deformation of the initial reference model therefore corresponds to a change in the position and/or of the shape of the teeth between the creation of the model from the initial time of the creation of the initial reference model and the later time. This change may have led to the appearance of regions of teeth which were initially embedded in the gum, or hidden by of other teeth, or to the appearance of regions of the gum which were not visible when the initial reference model was created.

The current reference model therefore exhibits "blank areas" in the regions not observable at the initial times. It is therefore incomplete and hence does not allow, in particular, a deformation of a tooth or of the gum in these regions to be detected later on. This problem is particularly critical when the current reference model is exploited for the fabrication of an orthodontic appliance, for example in the framework of a re-work of a defective treatment, or for the implementation of a post-treatment orthodontic brace.

There exists a need for a method allowing the blank areas of a model to be limited, in particular in the reference models described in WO 2016 066651.

One aim of the invention is to respond, at least partially, to this need.

SUMMARY OF THE INVENTION

The invention provides a method of enrichment of a reference model to be enriched representing a dental arch of a patient, said method comprising the following steps:

A) acquisition, under first real acquisition conditions, of a first current image of said arch displaying one region of said arch;
B) exploration of the reference model to be enriched in such a manner as to determine a first view of the reference model to be enriched, in a first direction of observation, or "first reference image", said first reference image exhibiting a maximum match with the first current image;
C) determination, by comparison of the first reference image and of the first current image, of a first orphan point represented on the first current image and not represented on the first reference image when the first current image is in a first register position in which it is superposed, in the space of the reference model to be enriched, with the first reference image;
D) addition, in the reference model to be enriched, of a point, referred to as "parent point", on a first straight line parallel to the first direction of observation and passing through the first orphan point in the first register position;
E) optionally, comparison of the reference model to be enriched with the enriched reference model.

Preferably, the position of the parent point on the first straight line is
(a) the closest position to a second straight line determined according to the following steps:
   acquisition, under second real acquisition conditions, of a second current image of said arch displaying said region of said arch;
   exploration of the reference model to be enriched in such a manner as to determine a second view of the reference model to be enriched, in a second direction of observation, or "second reference image", said second reference image exhibiting a maximum match with the second current image;
   determination of a second orphan point having the same coordinates as the first orphan point in a frame of reference common to the first and second current images, the second straight line being the straight line parallel to the second direction of observation and passing through the second orphan point in a second register position in which the second current image is superposed, in the space of the reference model to be enriched, with the second reference image; or
(b) determined as a function of an approximate distance with a surface and/or a defined approximate line, in the space of the reference model to be enriched.

As will be seen in more detail in the following part of the description, a method according to the invention allows a fast and reliable enrichment of the reference model.

A method according to the invention may furthermore notably comprise one or more of the following optional features:

in the embodiment (a), the common frame of reference is determined by at least three first noteworthy points on the first current image and three second noteworthy points on the second current image, each pair of a first noteworthy point and of a second noteworthy point representing the same noteworthy point of the arch;
a noteworthy point of the arch is a point exhibiting a particularity, preferably easily identifiable by an operator, preferably a point where a contour of the arch exhibits an atypical change, for example by forming an acute angle, or branches out;

in the embodiment (b), the parent point is positioned in such a manner as to minimize said distance with the approximate surface and/or the approximate line;

the approximate surface and/or the approximate line are determined by statistical methods or by means of a neural network;

the first and/or second reference image is/are sought by means of a metaheuristic method;

for determining at least one of said first and second reference images, virtual acquisition conditions are sought in which the observation of the reference model to be enriched supplies an image exhibiting a maximum match with said at least one of said first and second current images, respectively;

said reference image is determined according to the following steps:
  a. processing of the current image in order to generate at least one current map representing, at least partially, discriminating information;
  b. determination of virtual acquisition conditions to be tested;
  c. generation of a reference image for the reference model to be enriched under said virtual acquisition conditions to be tested, or "reference image to be tested";
  d. processing of the reference image to be tested so as to form at least one reference map representing said discriminating information;
  e. comparison of the current and reference maps in such a manner as to determine a value for a first evaluation function, said value for the first evaluation function depending on the differences between said current and reference maps;
  f. depending on the value of the first evaluation function, modification of the virtual acquisition conditions to be tested, then return to the step c. or definition of said reference image as being the reference image to be tested;

the discriminating information is chosen from within the group consisting of contour information, color information, density information, distance information, brightness information, saturation information, information on the reflections and on the combinations of all these pieces of information;

the determination of the virtual acquisition conditions to be tested is carried out by means of a metaheuristic method;

the reference model to be enriched is generated by a scan of said arch of the patient;

the steps B) to D) are executed, in a loop, for more than 5, preferably more than 10, preferably more than 100 pairs of first and second current images;

the steps B) to D) are executed, in a loop, for each point of the first current image not represented in the reference model to be enriched such as defined before the first occurrence of the step B);

at the step E), based on the comparison of the reference model to be enriched with the enriched reference model, a change in the shape and/or in the position of a tooth of the dental arch, and/or a loss of material resulting from an abrasion of said tooth are determined;

the first and second current images are acquired more than 2, more than 5 or more than 10 weeks before or after the generation of the reference model to be enriched.

A method according to the invention may in particular be implemented for enriching a current reference model obtained by deformation of an initial reference model, preferably according to the teaching of WO 2016 066651.

Such a method preferably comprises the following steps:
1) at an initial time, generation of a reference model of an arch of a patient, or "initial reference model";
2) at a current moment in time, acquisition of the said first and second current images;
3) deformation of the initial reference model in such a manner as to obtain a current reference model starting from which the first and second reference models that are the closest match with the first and second current images are respectively observable;
4) enrichment of the current reference model using said first and second reference images, according to the steps ii) to iv).

Preferably, at the step 3), the deformation of the initial reference model is determined by means of a metaheuristic method.

A method according to the invention may notably be implemented in the framework of a method for monitoring the positioning and/or the shape and/or the aspect of teeth of a patient such as that described in WO 2016 066651, incorporated by reference.

The invention also relates to:
  a computer program, and in particular, a specialized application for a mobile telephone, comprising program code instructions for the execution of one or more steps of an any given method according to the invention, when said program is executed by a computer,
  a storage medium on which such a program is recorded, for example a memory or a CD-ROM.

Definitions

A "patient" is a person for which a method according to the invention is implemented, independently of whether this person is following an orthodontic treatment or not.

An "orthodontist" is understood to be any person qualified to administer dental treatment, which also includes a dentist.

The term "orthodontic component" is understood to mean all or part of an orthodontic appliance.

A "model" is understood to mean a three-dimensional physical model. The distinction is made between "reference model to be enriched", prior to implementation of the method of the invention, and the "enriched reference model", resulting from the implementation of the method of the invention. A "current reference model" is a model obtained by optimal deformation of a "initial reference model" using images, as described in WO 2016 066651. A current reference model is a particular example of a reference model to be enriched.

An "image" is understood to mean a two-dimensional image, such as a photograph or an image taken from a film. An image is composed of pixels.

A "reference image" is a view of a "reference" model. According to the invention, a reference image is sought which has the best match with a current image. For this purpose, the space of the reference model is explored whilst observing this model, until the current image is substantially observed. In other words, if the current image is superposed as closely as possible with the view of the model thus obtained (reference image), outside of the blank areas, a substantially perfect superposition, said to be "in register", is obtained. The current image in register with said reference image, in the space of the model, is said to be in "register position". The observation of the current and reference images in register position allows, by transparency, the points of the current image which are not represented on the reference image, in other words the orphan points which are not represented in the reference model, to be identified.

The term "image of an arch", or "model of an arch", is understood to mean a representation of all or part of said arch.

The "conditions of acquisition" of an image define the position and the orientation in the space of an apparatus for acquisition of this image relative to the teeth of the patient (real acquisition conditions) or to a model of the teeth of the patient (virtual acquisition conditions), and preferably the calibration of this acquisition apparatus. Acquisition conditions are said to be "virtual" when they correspond to a simulation in which the acquisition apparatus is under said acquisition conditions (theoretical positioning and preferably calibration of the acquisition apparatus) with respect to a model.

Under virtual conditions of acquisition of a reference image, the acquisition apparatus may also be considered as "virtual". The reference image is indeed acquired by a dummy acquisition apparatus, having the characteristics of the "real" acquisition apparatus having been used for the acquisition of the real images, and in particular of the current images.

The "calibration" of an acquisition apparatus consists of all of the values of the calibration parameters. A "calibration parameter" is a parameter that is intrinsic to the acquisition apparatus (except for its position and its orientation) whose value influences the acquired image. Preferably, the calibration parameters are chosen from within the group formed by the aperture, the exposure time, the focal distance and the sensitivity.

"Discriminating information" is characteristic information which may be extracted from an image ("characteristic image"), conventionally by a digital processing of this image.

Discriminating information may take a variable number of values. For example, contour information may be equal to 1 or 0 if a pixel belongs to a contour or not. Brightness information may take a large number of values. The processing of the reference image allows the discriminating information to be extracted and quantified.

The discriminating information may be represented in the form of a "map". A map is thus the result of a processing of an image in order to display the discriminating information, for example the contour of the teeth and of the gums.

A point of an image (or of a map), for example a point of a tooth contour, comes from the projection of a point of the dental arch of the patient, in the direction of image capture when the image is taken (the direction of image capture being defined by the orientation of the objective lens of the image acquisition apparatus during this acquisition). The point of the model of the dental arch representing this point of the dental arch is referred to as "parent point" of the point of the image (or of a map).

In other words, the point of the image is the representation of the parent point under the conditions of acquisition of the image. In particular, the point of the current map is the representation of the parent point under the conditions of acquisition of the current image.

When a point of an image, for example a contour point, does not have a parent point in the model, it is said to be an "orphan". The model therefore has a blank area at the location of the missing parent point.

A parent point is at a location "compatible" with a point of an image when it is represented, on this image, by this point.

A "match" between two objects is a measure of the difference between these two objects. It is a "best match" when it results from an optimization in such a manner as to minimize said difference.

An object modified in order to obtain a best match may be classed as an "optimal" object.

Two images or "views" which exhibit a best match substantially show at least the same tooth, in the same manner. In other words, the representations of the tooth on these two images are substantially superposable.

The search for a reference image exhibiting a maximum match with a current image is carried out by seeking the virtual acquisition conditions of the reference image exhibiting a maximum match with the real conditions of acquisition of the current image.

By extension, a model exhibits a best match with an image when this model has been chosen from amongst several models since it allows a view exhibiting a maximum match with said image and/or when this image has been chosen from amongst several images since it exhibits a best match with a view of said model.

In particular, a current image is a best match with a reference model when a view of this reference model provides a reference image that best matches the current image.

The comparison between two images preferably results from the comparison of two corresponding maps. A "distance" conventionally refers to a measurement of the difference between two maps or between two images.

"Metaheuristic" methods are known optimization methods. They are preferably chosen within the group formed by
- evolutionary algorithms, preferably chosen from amongst: evolutionary strategies, genetic algorithms, differential evolution algorithms, distribution estimation algorithms, artificial immunity systems, the Shuffled Complex Evolution path re-composition, simulated annealing, ant colony algorithms, particle swarm optimization algorithms, taboo search, and the GRASP method;
- the kangaroo algorithm,
- the method of Fletcher and Powell,
- the sound-effects method,
- stochastic tunneling,
- hill climbing with random restarts,
- the cross-entropy method, and
- hybrid methods between the aforementioned metaheuristic methods.

The terms "comprising" or "having" or "exhibiting" should be interpreted in the non-restrictive sense, unless otherwise stated.

BRIEF DESCRIPTION OF THE FIGURES

Other features and advantages of the invention will become more clearly apparent upon reading the detailed description that follows and upon examining the appended drawing in which.

DETAILED DESCRIPTION

A method of enrichment according to the invention is designed to enrich a model. It may in particular be implemented in the framework of a method comprising steps 1) to 4).

Step 1) is for the development of an initial reference model modeling a dental arch of the patient. It preferably comprises one or more of the features of the step a) of WO 2016 066651, incorporated by reference.

The initial reference model is preferably created with a 3D scanner. Such a '3D' model may be observed along any give angle. An observation of the model, along a given angle and at a given distance, is called a "view" or "reference image".

Figure 4:
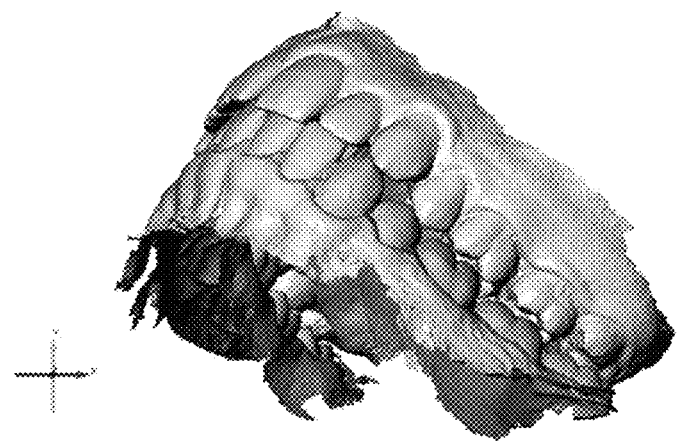
FIG. 4 shows one example of a reference image of an initial reference model.

FIG. 4 is one example of a reference image.

The initial reference model may be prepared based on measurements carried out on the teeth of the patient or on a molding of their teeth, for example a plaster molding.

Preferably, for each tooth, starting from the initial reference model, a model of said tooth, or "tooth model", is defined (FIG. 5). This operation, known per se, is also referred to as "segmentation of the initial reference model".

In the initial reference model, a tooth model is bounded by a gum edge which may be decomposed into an inner gum edge (on the inside of the mouth with respect to the tooth), an outer gum edge (oriented toward the outside of the mouth with respect to the tooth) and two lateral gum edges.

In the initial reference model, only the exposed surface on the outside may be scanned. For example, the surfaces of two adjacent teeth facing each other may be inaccessible to the scanner and cannot be represented. The same is true for the parts of teeth which are covered by the gum. The initial reference model does not therefore show the entirety of the teeth and of the gum. The "holes" in the model are called "blank areas". If a complete scan of the dental arch has been made, the initial reference model does not however display the blank areas.

The initial time at which the initial reference model is generated may in particular be a time preceding an active orthodontic treatment, for example less than 6 months, less than 3 months, or less than 1 month before the start of the treatment. The steps 1) to 3) are implemented in order to monitor the progress of the treatment between the initial time and the current time in the step 2).

The initial time may alternatively be a time at the end of active orthodontic treatment, for example less than 6 months, less than 3 months, or less than 1 month after the end of the treatment. The steps 1) to 3) are then implemented in order to monitor any re-occurrence of the problem.

Step 2) is for the acquisition, at a current moment in time, of current images intended to guide the modification of the initial reference model in order to define the current reference model, at the step 3). For the enrichment of this model, at least first and second current images of the arch must be acquired, under first and second real acquisition conditions showing the same region of said arch from different angles of observation.

The step 2) preferably comprises one or more of the features of the step b) of WO 2016 066651.

The acquisition of the current images is carried out by means of an image acquisition apparatus, preferably a mobile telephone.

The interval of time between the steps 1) and 2) may, for example, be longer than 1 week, than 2 weeks, than 1 month, than 2 months or than 6 months.

Figure 6A:
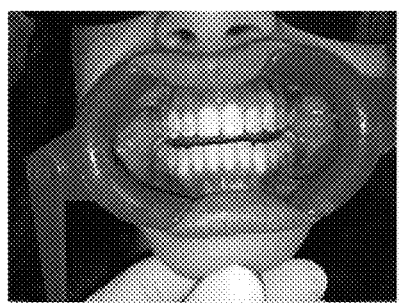
Figure 6B:
Figure 6B:
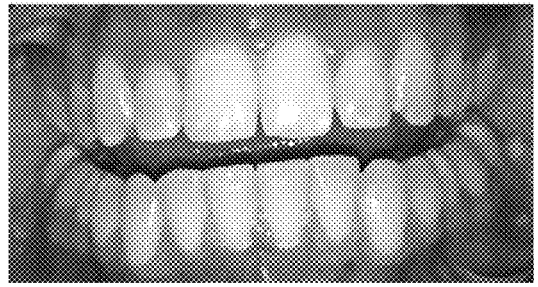
Figure 6C:
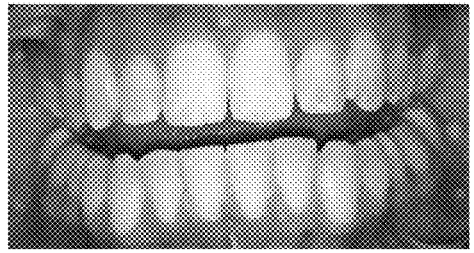
Figure 6D:
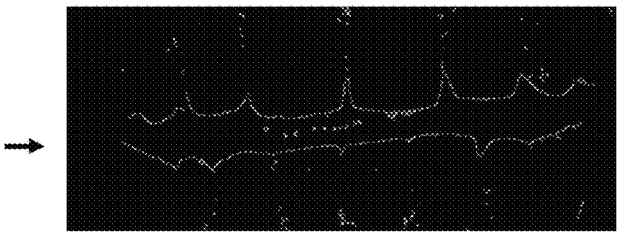

Preferably, a dental retractor 10 is used during the step 2), as shown in FIG. 6a. The retractor conventionally comprises a support having a flange extending around an opening and arranged in such a manner that the lips of the patient can rest in it leaving the teeth of the patient exposed through said opening.

Step 3) is for the generation of a current reference model exhibiting a maximum match with the current images.

Figure 3:
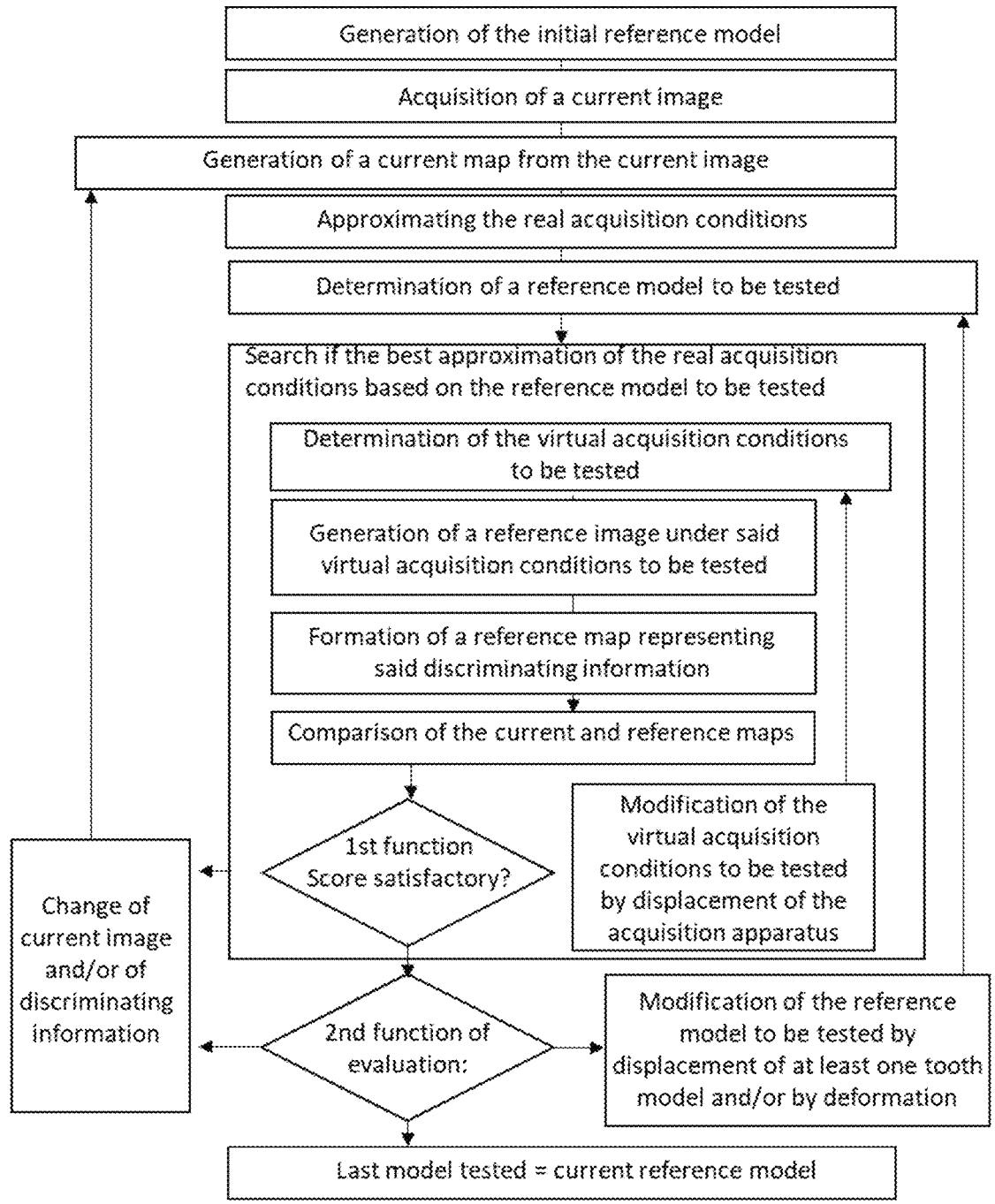
FIG. 3 shows a flow diagram illustrating a search for a current reference model starting from an initial reference model.

It preferably comprises one or more of the features of the steps c), d) and e) of WO 2016 066651, as illustrated in FIG. 3.

At the step 3), each current image is analyzed in such a manner as to form, for each current image, a current map relating to at least one discriminating piece of information.

Figure 5A:
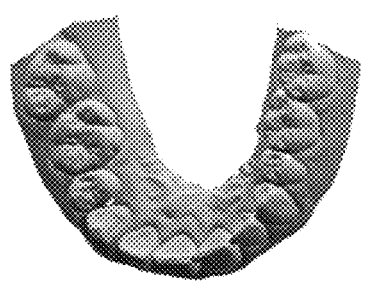
FIG. 5 (5a-5d) illustrates a processing operation for determining the tooth models in an initial reference model, as described in WO 2016 066651, FIG. 6 (6a-6d) illustrates the acquisition of a current image by means of a retractor, an operation for cutting out this image, and the processing of a current image allowing the contour of the teeth to be determined, as described in WO 2016 066651.
Figure 5B:
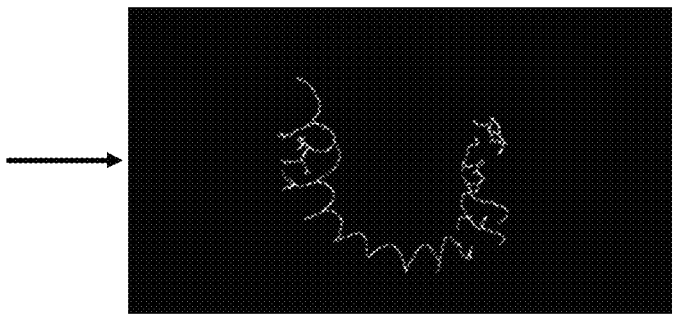
Figure 5C:
Figure 5D:
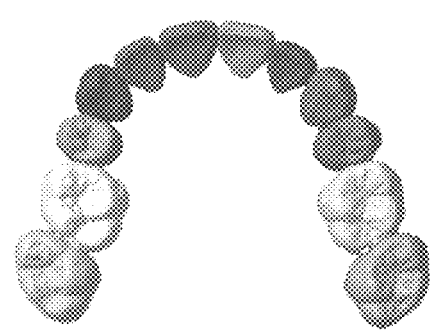

A current map shows discriminating information in the reference frame of the current image. For example, FIG. 5b is a current map relating to the contour of the teeth obtained from the current image in FIG. 5a.

The discriminating information is preferably chosen from within the group consisting of contour information, color information, density information, distance information, brightness information, saturation information, information on the reflections and of combinations of all these pieces of information.

Those skilled in the art will know how to process a current image in order to display the discriminating information.

Subsequently, for each current image, virtual acquisition conditions approximating the real acquisition conditions during the step 1) are preferably roughly determined. In other words, the position of the image acquisition apparatus with respect to the teeth is estimated at the moment when it took the current image (position of the acquisition apparatus in the space and orientation of this apparatus). This rough evaluation advantageously allows the number of tests under virtual acquisition conditions during the following operations to be limited, and hence allows these operations to be considerably accelerated.

In order to perform this rough evaluation, one or more heuristic rules are preferably used. For example, preferably, the conditions which correspond to a position of the image acquisition apparatus behind the teeth or at a distance from the teeth of greater than 1 m are excluded from the virtual acquisition conditions able to be tested during the following operations.

Figure 7:
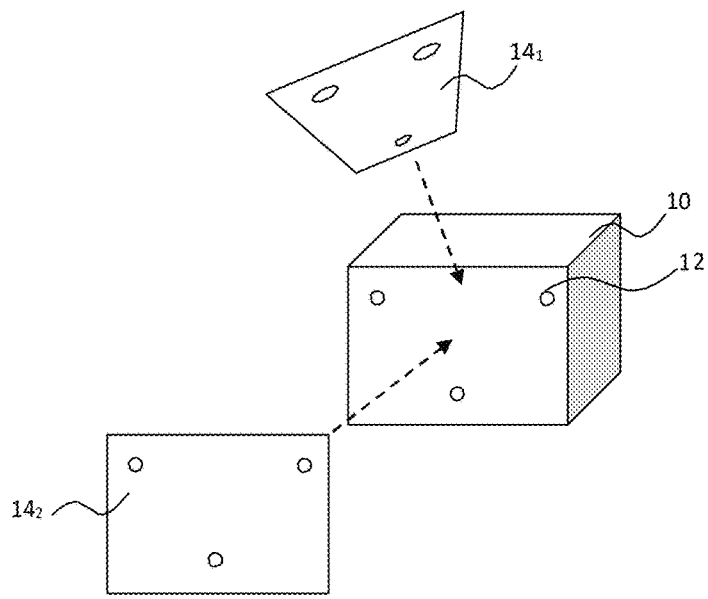
FIG. 7 illustrates schematically the relative position of reference positioning marks 12 of a retractor 10 on current images $14_1$ and $14_2$, in the directions of observation shown by dashed lines.

In one preferred embodiment, as illustrated in FIG. 7, reference positioning marks shown on the current image are used, and in particular reference positioning marks 12 of the retractor, so as to determine a substantially conical region of the space bounding virtual acquisition conditions able to be tested during the following operations, or "test cone".

In practice, at least three non-aligned reference positioning marks 12 are preferably disposed on the retractor 10, and their relative positions on the retractor are accurately measured.

The reference positioning marks are subsequently identified on the current image, as previously described. Simple trigonometric calculations allow the direction in which the current image has been taken to be approximately determined.

Subsequently, for each current image, a current reference model corresponding to the positioning and/or to the shape of the teeth when the current image was acquired is more precisely sought, the search being preferably carried out by means of a metaheuristic method, preferably evolutionistic, preferably by simulated annealing.

This search is preferably carried out based on the roughly evaluated virtual acquisition conditions.

The objective is to modify the initial reference model until a current reference model is obtained which exhibits a best match with the current image. Ideally, the current reference model is accordingly a reference model from which the current image could have been taken if this model of the arch had been the arch itself.

A succession of reference models "to be tested" is therefore tested, the choice of a reference model to be tested being preferably dependent on the level of correspondence of the reference models "to be tested" previously tested with the current image. This choice is preferably made according to a known method of optimization, in particular chosen from amongst the metaheuristic, preferably evolutionist, methods of optimization, in particular the simulated annealing methods.

Preferably, the search comprises
a first optimization operation allowing virtual acquisition conditions to be sought corresponding, at best, to the real acquisition conditions in a reference model to be tested determined based on the initial reference model, and
a second optimization operation allowing the reference model corresponding, at best, to the positioning of the teeth of the patient during the acquisition of the current image at the step 1) to be sought by testing a plurality of said reference models to be tested.

Preferably, a first optimization operation is carried out for each test of a reference model to be tested during the second optimization operation.

Preferably, the first optimization operation and/or the second optimization operation, preferably the first optimization operation and the second optimization operation implement a metaheuristic method, preferably evolutionist, preferably a simulated annealing.

Preferably, the search for a current reference model, for each current image, corresponding to the step e) of WO 2016 066651, comprises the following steps:
e1) definition of a reference model to be tested as being the initial reference model then,
e2) according to the following steps, test of virtual acquisition conditions with the reference model to be tested in order to closely approximate said real acquisition conditions;
e21) determination of virtual acquisition conditions to be tested;
e22) generation of a reference image for the reference model to be tested under said virtual acquisition conditions to be tested;
e23) processing of the reference image in order to form at least one reference map representing, at least partially, the discriminating information;
e24) comparison of the current and reference maps in such a manner as to determine a value for a first evaluation function, said value for the first evaluation function depending on the differences between said current and reference maps and corresponding to a decision to continue or to stop the search of virtual acquisition conditions approximating said real acquisition conditions with more exactitude than said virtual acquisition conditions to be tested determined at the last occurrence of the step e21);
e25) if said value for the first evaluation function corresponds to a decision to continue said search, modification of the virtual acquisition conditions to be tested, then return to the step e22);
e3) determination of a value for a second evaluation function, said value for the second evaluation function depending on the differences between the current and reference maps under the virtual acquisition conditions best approximating said real acquisition conditions and resulting from the last occurrence of the step e2), said value for the second evaluation function corresponding to a decision to continue or to stop the search for a reference model approximating the positioning of the teeth when the current image was acquired with more exactitude than said reference model to be tested used at the last occurrence of the step e2) and, if said value for the second evaluation function corresponds to a decision to continue said search, modification of the reference model to be tested by displacement of one or more models of teeth, then continue at the step e2).

At the step e1), it is determined that the reference model to be tested is the initial reference model during the first execution of the step e2).

The step e2) starts by determining virtual acquisition conditions to be tested, in other words a virtual position and orientation likely to correspond to the real position and orientation of the acquisition apparatus when the current image was captured, but also, preferably, a virtual calibration likely to correspond to the real calibration of the acquisition apparatus when the current image was captured.

Subsequently, the image acquisition apparatus is virtually configured under the virtual acquisition conditions to be tested in order to acquire a reference image for the reference model to be tested under these virtual acquisition conditions to be tested. The reference image therefore corresponds to the image that the image acquisition apparatus would have taken if it had been placed, with respect to the reference model to be tested, and optionally calibrated, under the virtual acquisition conditions to be tested (step e22)).

If the current image has been taken while the position of the teeth was exactly that in the reference model to be tested, and if the virtual acquisition conditions are exactly the real acquisition conditions, the reference image is therefore exactly superposable onto the current image. The differences between the current image and the reference image result from errors in the evaluation of the virtual acquisition conditions (if they do not exactly correspond to the real acquisition conditions) and from differences in positioning of the teeth between the step 2) and the reference model to be tested.

In order to compare the current and reference images, the discriminating information from these two images is compared. More precisely, a reference map representing the discriminating information is formed (step e23) based on the reference image).

The current and reference maps, both relating to the same discriminating information, are subsequently compared and the difference between these two maps is evaluated by means of a score. For example, if the discriminating information is the contour of the teeth, the average distance may be compared between the points of the contour of the teeth which appears on the reference image and the points of the corresponding contour which appears on the current image, the score being higher the shorter this distance.

Preferably, the virtual acquisition conditions comprise the calibration parameters for the acquisition apparatus. The score will be higher the closer the values of the calibration parameters tested are to the values of the calibration parameters of the acquisition apparatus used when the current image was acquired. For example, if the optical aperture tested is far from that of the acquisition apparatus used when the current image was acquired, the reference image blurred regions and sharp regions which do not correspond to the blurred regions and to the sharp regions of the current image. If the discriminating information is the contour of the teeth, the current and reference maps will not therefore show the same contours and the score will be low.

The score may be for example a correlation coefficient.

The score is subsequently evaluated by means of a first evaluation function. The first evaluation function allows it to be decided whether the cycling on the step e2) is to be continued or stopped. The first evaluation function may for example be equal to 0 if the cycling has to be stopped or be equal to 1 if the cycling has to be continued.

The value of the first evaluation function may depend on the score achieved. For example, it may be decided to continue the cycling on the step e2) if the score does not exceed a first threshold. For example, if an exact correspondence between the current and reference images leads to a score of 100%, the first threshold may, for example, be 95%. It goes without saying that, the higher the first threshold, the better will be the precision of the evaluation of the virtual acquisition conditions if the score can exceed this first threshold.

The value of the first evaluation function may also depend on scores obtained with virtual acquisition conditions tested previously.

The value of the first evaluation function may also depend on random parameters and/or on the number of cycles of the step e2) already carried out.

In particular, it is possible that, in spite of the repetition of the cycles, virtual acquisition conditions cannot be found that are sufficiently close to the real acquisition conditions for the score to reach said first threshold. The first evaluation function may then lead to the decision to abandon the cycling even though the best score obtained has not reached said first threshold. This decision may result, for example, from a number of cycles greater than a predetermined maximum number.

A random parameter in the first evaluation function may also allow tests of new virtual acquisition conditions to continue, even though the score appears satisfactory.

The evaluation functions conventionally used in the metaheuristic methods of optimization, preferably evolutionist, in particular in the simulated annealing methods, may be used for the first evaluation function.

If the value of the first evaluation function indicates that it is decided to continue the cycling on the step e2), the virtual acquisition conditions to be tested are modified (step e25)) and a cycle is repeated (step e2)) which consists in forming a reference image and a reference map, then in comparing this reference map with the current map in order to determine a score.

The modification of the virtual acquisition conditions corresponds to a virtual displacement in the space and/or to a modification of the orientation and/or, preferably, to a modification of the calibration of the acquisition apparatus.

This modification may be random, as long as the new virtual acquisition conditions to be tested still however belong to the set determined during the rough evaluation. The modification is preferably guided by heuristic rules, for example favoring the modifications which, according to an analysis of the preceding scores obtained, appears the most likely to increase the score.

The cycling on e2) carries on until the value of the first evaluation function indicates a decision to come out of this cycling and to proceed to the step e3), for example if the score reaches or exceeds said first threshold.

The optimization of the virtual acquisition conditions at the step e2) is preferably carried out using a metaheuristic method, preferably evolutionist, preferably a simulated annealing algorithm. Such an algorithm is well known for non-linear optimization.

If the cycling on the step e2) has ended without a satisfactory score having been able to be obtained, for example without the score having been able to reach said first threshold, the method may be terminated (failure situation) or a new step 2) may be launched, with new discriminating information and/or with a new current image. The method may also continue with the virtual acquisition conditions corresponding to the best score achieved. A warning may be raised in order to inform the user of the error on the result.

If the cycling on the step e2) has ended when a satisfactory score has been obtained, for example because the score has reached, or exceeded said first threshold, the virtual acquisition conditions correspond substantially to the real acquisition conditions.

Preferably, the virtual acquisition conditions comprise the calibration parameters of the acquisition apparatus. The method conduit thus allows the values of these parameters to be evaluated without it being necessary to know the nature of the acquisition apparatus or its adjustment. The acquisition of the current images may therefore be carried out without any particular precaution, for example by the patient themselves by means of their mobile telephone.

Furthermore, the search for the real calibration is carried out by comparing a current image with views of a reference model to be tested under virtual acquisition conditions that are tested. Advantageously, it is not necessary for the current image to display a standard calibration gauge, in other words a gauge whose characteristics are precisely known allowing the calibration of the acquisition apparatus to be determined.

As can now be clearly seen, the current images are not used to create a totally new current three-dimensional model, but only to modify the initial very precise reference model. A totally new current three-dimensional model created from simple photographs taken without any particular precautions would indeed be too imprecise for a comparison with the initial reference model to be able to lead to conclusions on the movement of the teeth.

Even if the virtual acquisition conditions correspond exactly to the real acquisition conditions, differences may subsist between the current and reference images if teeth move between the creation of the initial reference model and the acquisition of the current images. The correlation between the current and reference images may then be further improved by repeating the step e2) after modification of the reference model to be tested by displacement of one or more models of teeth (step e3)); this is the object of the second optimization.

The search for the reference model best approximating the positioning of the teeth when the current image was acquired may be carried out like the search for the virtual acquisition conditions best approximating the real acquisition conditions (step e2)).

In particular, the score is evaluated by means of a second evaluation function. The second evaluation function allows it to be decided whether the cycling on the steps e2) and e3) is to be continued or stopped. The second evaluation function may for example be equal to 0 if the cycling has to be stopped or be equal to 1 if the cycling has to be continued.

The value of the second evaluation function preferably depends on the best score obtained with the reference model to be tested, in other words on the differences between the current and reference maps, under the virtual acquisition conditions best approximating said real acquisition conditions.

The value of the second evaluation function may also depend on the best score obtained with one or more reference models tested previously.

For example, it may be decided to continue the cycling if the score does not exceed a second minimum threshold. The value of the second evaluation function may also depend on random parameters and/or on the number of cycles in the steps e2) and e3) already carried out.

The evaluation functions conventionally used in the metaheuristic methods of optimization, preferably evolutionist, in particular in the simulated annealing methods, may be used for the second evaluation function.

If the value of the second evaluation function indicates that the decision is to continue the cycling on the steps e2) and e3), the reference model to be tested is modified and a cycle (steps e2) and e3)) is repeated with the new reference model to be tested.

The modification of the reference model to be tested corresponds to a displacement of one or more models of teeth. This modification may be random. The modification is preferably guided by heuristic rules, for example by favoring the modifications which, according to an analysis of the preceding scores obtained, appear to be the most likely to increase the score.

Preferably, the displacement of a tooth model is sought which has the greatest impact on the score, the reference model to be tested is modified by displacing this tooth model, then the cycling on the steps e2) and e3) is continued in such a manner as to optimize the score. From amongst the other tooth models, that which has the greatest impact on the improvement of the score may subsequently be sought, and the optimum displacement of this other tooth model on the score again be sought. This process may thus be continued with each tooth model.

Subsequently, it is possible to repeat a cycle over the whole set of tooth models and to continue this cycle until a score higher than the second threshold is obtained. Of course, other strategies may be used for displacing one or more tooth models in the reference model to be tested and to search for the maximum score.

The cycling on the steps e2) and e3) is continued until the value of the second evaluation function indicates a decision to come out of this cycling and to continue to the step f), for example if the score reaches or exceeds said second threshold.

The cycling on the steps e2) and e3) advantageously allows the evaluation of the calibration parameters of the acquisition apparatus at the step 1) to be improved.

The search for a reference model with a cycling on the steps e2) and e3) for seeking the positions of the tooth models that optimize the score is preferably carried out using a metaheuristic method, preferably evolutionist, preferably a simulated annealing algorithm. Such an algorithm is well known for non-linear optimization.

If the cycling on the steps e2) and e3) has been abandoned without a satisfactory score having been able to be obtained, for example without the score having been able to reach said second threshold, the method may be stopped (failure situation) or re-started from the start of step 3) with new discriminating information and/or with a new current image.

If it is decided to re-start the method at the start of step 3) based on another piece of discriminating information and/or on another current image because the first threshold or the second threshold has not been reached, the choice of the new discriminating information and/or of the new current image may depend on the scores obtained previously, in order to favor the discriminating information and/or the current image which, in view of these scores, appears the most promising.

A new discriminating information, obtained for example by combining other discriminating information already tested, may be used. Where appropriate, it may also be requested to acquire one or more new current images. Preferably, indications are supplied allowing the positioning of the acquisition apparatus for the capture of this new current image to be guided. For example, it may be indicated to the patient that they should take a photo of the right-hand part of their lower arch.

If the cycling on the steps e2) and e3) has been abandoned without a satisfactory score having been able to be obtained, a warning may be raised in order to inform the user of the error on the result.

If the cycling on the steps e2) and e3) has been stopped where a satisfactory score has been obtained, for example because the score has reached, or exceeded said second threshold, the virtual acquisition conditions correspond substantially to the real acquisition conditions and the models of teeth in the reference model obtained (referred to as "current reference model") are substantially in the position of the teeth of the patient at the time of the step 2).

The fabrication of the current reference model at the step 2) is advantageously possible without any particular precaution, notably because the real positioning of the teeth is measured with a current reference model which results from a deformation of the initial reference model in order for the current images to be deformed views of the initial reference model.

At the end of the step 3), the current reference model substantially matches the current images. It is then possible to make precise measurements on the positioning of the teeth and/or on their shape.

Furthermore, the step 3) leads, by means of first and second current maps, and of first and second reference maps, to the determination of the first and second virtual acquisition conditions allowing, by observing the current reference model, first and second reference images to be obtained exhibiting a maximum match with the first and second current images, respectively.

Figures 1A, 1B, 1C:
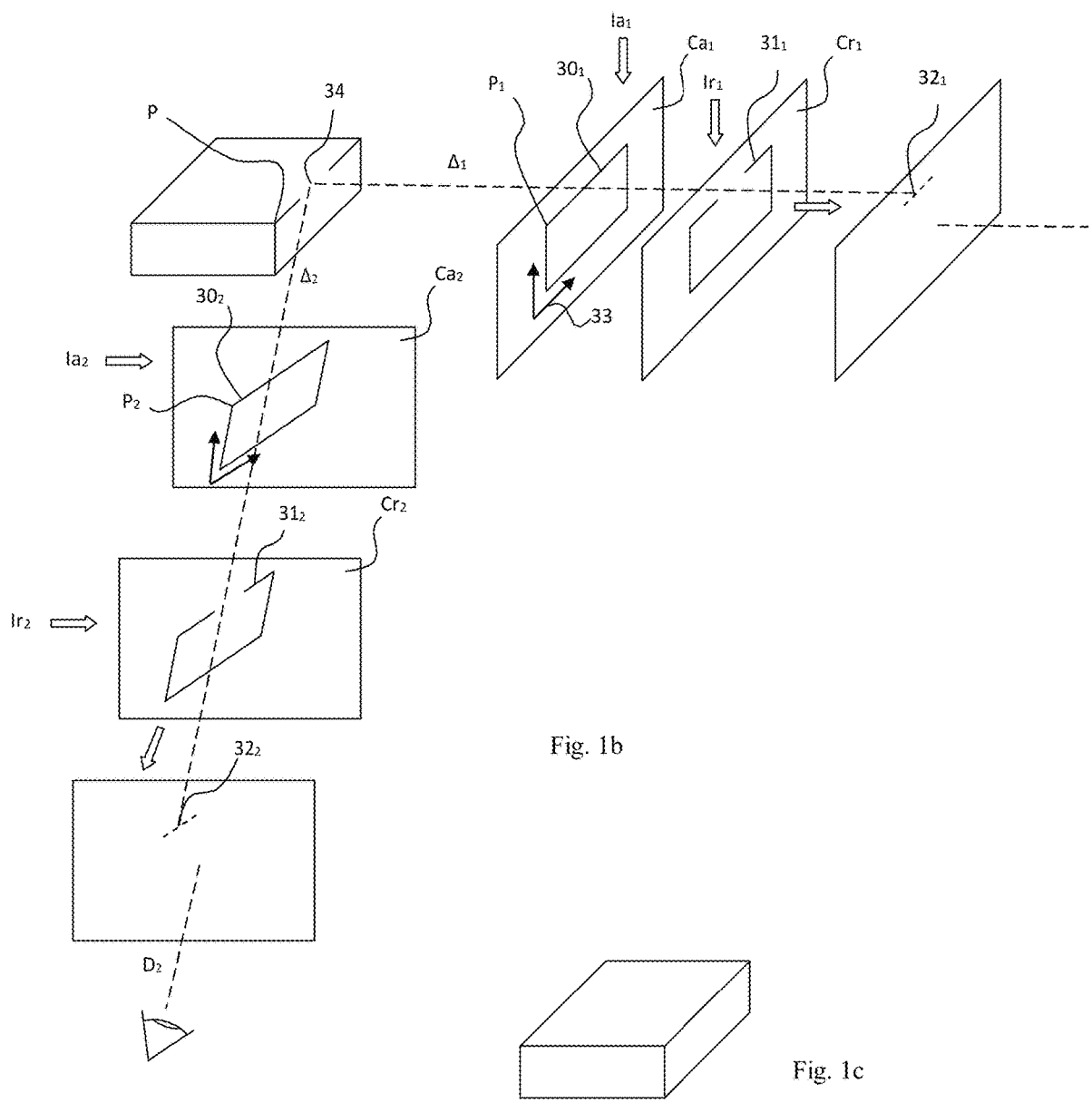
FIG. 1 (1a-1c) shows, schematically, the various steps of an enrichment of a model.
Figure 2:
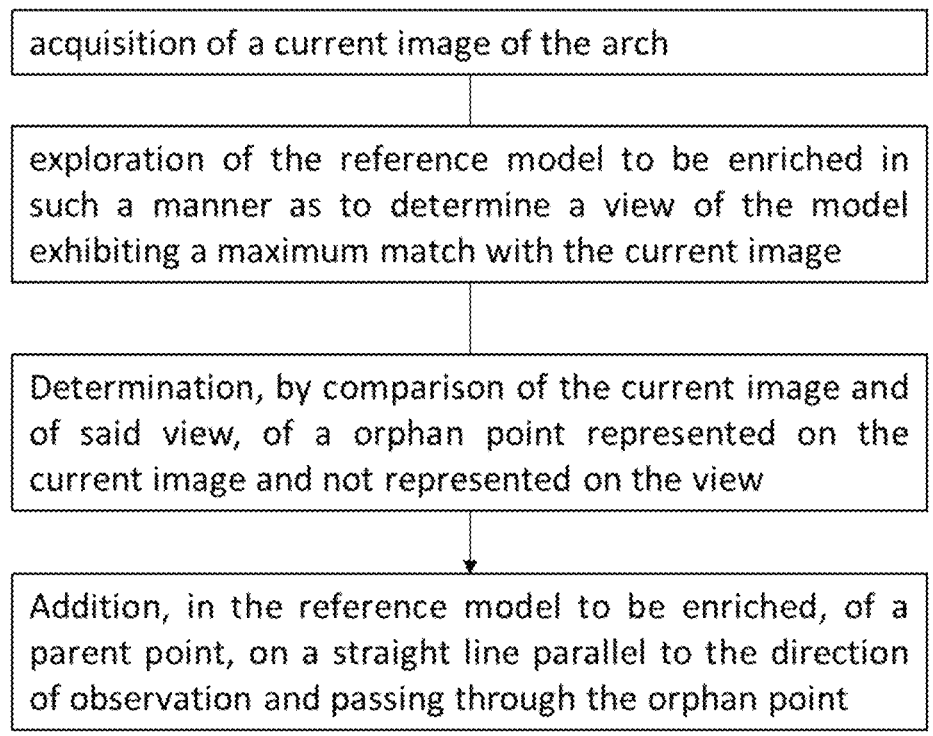
FIG. 2 shows a flow diagram illustrating the implementation of a method according to the invention.

However, the current reference model 20 (shown very schematically in FIG. 1a) may comprise blank areas 22, resulting for example from a retractation of the gum or from a displacement of a tooth having led to exposing a surface which it was not possible to scan when the initial reference model was created. Visually, the current reference model thus exhibits holes, for example when the contour of a tooth is interrupted near to the gum.

At the step 4), the current reference model is enriched by means of information contained in the first and second current images and which was not available when the initial reference model was created.

In one embodiment, the method according to the invention comprises the following steps:
i) acquisition of first and second images of said arch, referred to as "current images", under first and second real acquisition conditions showing the same region of said arch under different angles of observation;
ii) comparison of the first current image with a first reference image for the reference model to be enriched, exhibiting a maximum match with the first current image, in such a manner as to identify at least one point of the first current image not shown in the reference model to be enriched, or "first orphan point";
iii) comparison of the second current image with a second reference image for the reference model to be enriched, exhibiting a maximum match with the second current image, in such a manner as to identify a point of the second current image representing the same point of the arch as the first orphan point, or "second orphan point";
iv) addition, in the reference model to be enriched, of a point, called "parent point", at a location compatible with the first and second orphan points, in such a manner as to obtain an enriched reference model.

The step i) comprises one or more features of the step 2).

FIG. 1 illustrates a step 4) which comprises steps ii) to iv).

The steps ii) and iii) illustrate the embodiment (a).

At the step ii), the first current image is compared with the first reference image, in such a manner as to identify the first orphan points, in other words appearing on the first current image and not appearing in the current reference model.

Preferably, this comparison uses the first current and reference maps.

In the embodiment in FIG. 1, the discriminating information is contour information.

The first current map $Ca_1$, obtained from the first current image $Ia_1$, shows a first closed "current" contour $30_1$. The first reference image $Ir_1$ is obtained by observation of the current reference model 20 under the first virtual acquisition conditions simulating the real acquisition conditions having allowed the first current image $Ia_1$ to be acquired. Its processing results in the first reference map $Cr_1$ which displays a first interrupted "reference" contour $31_1$. The interruption of the first reference contour indeed corresponds to the blank area 22.

In order to compare the first current image with the first reference image, the first current map $Ca_1$ and reference map $Cr_1$ are superposed, which displays a set of first orphan points $32_1$, shown as dashed lines.

The identification of the first orphan points $32_1$ does not however allow the position of the respective points parents 34 to be determined in the current reference model 20. In particular, for a first orphan point, it is not possible to precisely identify the position of the parent point along the first straight line $\Delta_1$ passing through the first orphan point (while the first current image is in its register position with the first reference image in the space of the current reference model, as shown in FIG. 1) and parallel to the first direction of observation $D_1$ of the current reference model when the first reference image is acquired.

At the step iii), the same operations are carried out as at the step ii), but with the second current image $Ia_2$.

The second current map $Ca_2$, obtained from the second current image $Ia_2$, shows a second closed current contour $30_2$. The second reference image $Ir_2$ is obtained by observation of the current reference model 20 in the second virtual acquisition conditions simulating the real acquisition conditions having allowed the acquisition of the second current image $Ia_2$. Its processing results in a second reference map $Cr_2$ which displays a second interrupted reference contour $31_2$. The interruption of the second reference contour corresponds to the blank area 22.

In order to compare the second current image with the second reference image, the second current map $Ca_2$ and reference map $Cr_2$ are superposed, which displays a set of second orphan points $32_2$, shown as dashed lines.

The first and second current images have been chosen to represent the same region of the arch (the region which produces the blank area of the current reference model). Their analysis has led to first and second reference images which represent the same blank area 22 and, at least close to the blank area, the same points of the arch. It is therefore possible to identify, on the first and second current images, a pair of first and second noteworthy points, $P_1$ and $P_2$ respectively, which represent the same noteworthy point P of the arch, for example an end of a tooth or a point of contact between two teeth, in the region close to the blank area. Three such pairs allow a reference frame 33 common to the first and second current images to be defined. In other words, near to the blank area, the same point of the arch is represented on the first and second current images by first and second points which have substantially, or even exactly, the same coordinates in this reference frame.

In particular, contour points may be used as noteworthy points for defining the reference frame 33.

In an equivalent manner, the determination of the reference frame 33 may also be carried out by means of the current and reference maps.

There exists a bias resulting from the different perspectives between the first and second current images. The effect of this bias may however be reduced by using points close to the blank area for establishing the reference frame 33.

By means of this reference frame 33, for each first orphan point, a second orphan point having the same coordinates or substantially identical coordinates is sought. The first and second orphan points are thus associated in order to define pairs which each allow a parent point 34 to be defined.

More precisely, the parent point is at the intersection between the first straight line $\Delta_1$ and the second straight line $\Delta_2$ passing through the second orphan point (while the second current image is in the second register position with the second reference image in the space of the current reference model) and parallel to the second direction of observation $D_2$ of the current reference model when the second reference image is acquired.

If, for a first orphan point, no second orphan point having the same coordinates or substantially identical coordinates is found, this first orphan point is abandoned and the step ii) is repeated in order to determine another first orphan point.

The steps ii) and iii) are preferably carried out for all the first orphan points.

The embodiment (b) advantageously allows the parent point to be defined without making use of a second current image.

The position of the parent point on the first straight line $\Delta_1$ is determined by taking into account the environment of the blank area from which the first orphan point comes.

Preferably, in the blank area, an approximate surface extending between the edges of the blank area is constructed. The approximate surface may be plane. Preferably, the approximate surface depends on the shape of the surface of the current reference model around the blank area. For example, the approximate surface may be determined so as to join to the surface of the current reference model around the blank area without forming a sharp edge. Preferably again, the approximate surface is determined statistically or by artificial intelligence based on historical data, acquired prior to the implementation of the method of the invention.

For example, if the blank area relates to a tooth, for example a canine, it is possible to establish the probable shape of this tooth by examining the known "historical" shapes of teeth of the same type (canines). According to the embodiment (b), an approximate surface for a region of the tooth is thus established so that it is in coherence with the historical data.

The historical data may in particular comprise information, preferably tooth or arch models, for more than 100, more than 1000 or more than 10,000 patients.

The artificial intelligence conventionally uses a 'deep learning' device, in the form of a neural network trained with the historical data, which constitute a "learning base". A neural network or "artificial neuronal network", is a set of algorithms well known to those skilled in the art.

The neural network may in particular be chosen from amongst:
  the networks specialized in the classification of images, called "CNN" ("Convolutional neural network"), for example
    AlexNet (2012)
    ZF Net (2013)
    VGG Net (2014)
    GoogleNet (2015)
    Microsoft ResNet (2015)
    Caffe: BAIR Reference CaffeNet, BAIR AlexNet
    Torch: VGG_CNN_S, VGG_CNN_M, VGG_CNN_M_2048, VGG_CNN_M_10 24, VGG_CNN_M_128, VGG_CNN_F, VGG ILSVRC-2014 16-layer, VGG ILSVRC-2014 19-layer, Network-in-Network (Imagenet & CIFAR-10)
    Google: Inception (V3, V4).
  the networks specialized in the localization, and detection of objects in an image, the Object Detection Network, for example:
    R-CNN (2013)
    SSD (Single Shot MultiBox Detector: Object Detection network), Faster R-CNN (Faster Region-based Convolutional Network method: Object Detection network)
    Faster R-CNN (2015)
    SSD (2015).
The list hereinabove is non-limiting.

The training of a neural network conventionally consists in activating the neurons composing it. The interconnection of these neurons subsequently defines the architecture of the network.

For example, when the historical data are arch models, the values of the parameters of the network are sought which, when these arch models, said to be "historical", are subjected to the neural network parameterized with said values, allow it to determine approximate arch models which come as close as possible to the historical arch models. The approximate arch models may thus be used to define approximate surfaces or approximate lines, in particular contour lines.

Alternatively, or as a complement to the approximate surface, an approximate line, for example meeting the ends of a contour interrupted by the blank area, may be constructed in the blank area. The shape of the approximate line is preferably determined by statistical analysis or by artificial intelligence using historical data, as explained hereinabove.

Preferably, the position of the parent point is determined in such a manner as to minimize the distance between the parent point and the first straight line $\Delta_1$.

At the step iv), the parent points are added to the current reference model.

The location, in other words the position in the space, of a parent point may be easily determined. This is because a parent point is at the intersection of the straight lines $\Delta_1$ and $\Delta_2$ passing through the first and second orphan points, respectively, and parallel to the directions of observation of the current reference model for obtaining the first and second current images, respectively. Such a location is compatible with the first and second orphan points.

If the reference model were really said arch, the representation of the parent point on the first and second current images would therefore be composed of the first and second orphan points.

Preferably, a parent point 34 is added for each pair of first and second orphan points.

The current reference model may thus be completed.

Preferably, the initial reference model is also enriched as a consequence. For this purpose, it suffices to re-displace the models of teeth from their position in the current reference model to their position in the initial reference model, in other words to carry out the inverse displacement of that carried out in order to define the current reference model.

The enrichment of the initial reference model is however only possible for the contours of teeth. Since the soft tissues such as the gums are deformable, it is indeed not possible to determine with precision how they have changed between the initial time and the current time.

The method is preferably executed for several pairs of first and second current images, which, advantageously, improves the enrichment.

In the embodiment (b), the parent point may advantageously be found using only the first image.

A method according to the invention may further comprise, after the step 4), a step 5) consisting, for each tooth model, in comparing the positionings of the tooth models in the initial reference model and in the current reference model, in order to determine the movement of the teeth between the steps 1) and 2), and/or in comparing the shapes of the initial reference model and of the current reference model in order to determine the deformation and/or the movement of teeth between the steps 1) and 2).

As will now be clearly apparent, the invention provides a method allowing the enrichment of a reference model to be enriched, and in particular a current reference model obtained by deformation of an initial reference model. Advantageously, this enrichment does not require a new scan of the teeth to be performed and hence does not oblige the patient to make a new appointment with the orthodontist.

The enrichment of the current reference model advantageously allows the movement and/or the deformation of a region of the dental arch to be monitored which had not been scanned when the initial reference model was created.

It goes without saying that the invention is not limited to the embodiment described in detail and illustrated. The invention could, in particular, be implemented outside of the framework of the method described in WO 2016 066651.

The method according to the invention may be used to enrich a reference model to be enriched, notably so that it is more complete and thus provides more information on the dental situation of the patient at the time when this reference model to be enriched has been created.

In particular, a blank area is an area of the reference model to be enriched for which a point of a current image, in particular a point of the contour of a tooth, is not shown whereas, according to a comparison of the current image and of the reference model to be enriched, it should appear in it. At the location intended for this point, the reference model to be enriched therefore exhibits a "hole". As explained hereinabove, the hole may result from the fact that it has not been possible to scan the corresponding point of the tooth when the reference model to be enriched was created. The invention may therefore be implemented in order to enrich a model produced by an incomplete scan, for example because a part of the teeth was masked during the scan.

The method according to the invention may be also used to adapt a reference model to be enriched in order for it to better correspond to an orthodontic situation which has changed.

The hole in the reference model to be enriched may, in particular, result from the fact that the position and/or the shape of the tooth has/have changed between the initial time and the current time, for example because the tooth has been subjected to an abrasion, for example during an orthodontic treatment. The invention may then be implemented in order to evaluate a modification of the shape or of the position of a tooth between the creation of the reference model to be enriched and the step i) for acquisition of the current images. The current images may thus be images of a tooth whose shape and/or position has/have changed. The method allows an enriched reference model, representing the contour of the tooth at the step i), to be constructed using a reference model to be enriched representing the tooth in its initial position or shape. In one preferred embodiment, the enriched reference model is compared with the reference model to be enriched, which advantageously allows the movement and/or the loss of material resulting from an abrasion to be evaluated.

In one embodiment, the current images are acquired for example more than 2, more than 5 or more than 10 weeks prior to the generation of the reference model to be enriched. For example, the patient may take photos of their teeth then, for example several months after, a reference model to be enriched may be generated. The enrichment of the reference model to be enriched then advantageously allows a reference model to be created at the time when the current images have been acquired. Advantageously, the method thus allows models of past dental situations to be created.

Lastly, the patient is not limited to a human being. In particular, an enrichment method according to the invention may be used for another animal.

The invention claimed is:

1. A computer non-transitory medium storing a computer program comprising code instructions for the execution of a method of enrichment of a reference model to be enriched representing a dental arch of a patient, when said program is run by a computer, said method comprising the following steps:
   B) exploration of the reference model to be enriched in such a manner as to determine a first view of the reference model to be enriched, in a first direction of observation, or "first reference image", said first reference image exhibiting a maximum match with the first current image;
   C) determination, by comparison of the first reference image and of a first current image of said arch displaying one region of said arch, of a first orphan point represented on the first current image and not represented on the first reference image when the first current image is in a first register position in which it is superposed, in the space of the reference model to be enriched, with the first reference image, said first current image has been acquired under first real acquisition conditions;
   D) addition, in the reference model to be enriched, of a point, referred to as "parent point", on a first straight line parallel to the first direction of observation and passing through the first orphan point in the first register position.

2. Computer non-transitory medium according to claim 1, in which the position of the parent point on the first straight line:
   (a) is the closest position of a second straight line determined according to the following steps:
      acquisition of a second current image of said arch under second real acquisition conditions displaying said region of said arch;
      exploration of the reference model to be enriched in such a manner as to determine a second view of the reference model to be enriched, in a second direction of observation, or "second reference image", said second reference image exhibiting a maximum match with the second current image;
      determination of a second orphan point having the same coordinates as the first orphan point in a reference frame common to the first and second current images, the second straight line being the straight line parallel to the second direction of observation and passing through the second orphan point in a second register position in which the second current image is superposed, in the space of the reference model to be enriched, with the second reference image;
   or
   (b) is determined as a function of a distance with an approximate surface and/or an approximate line defined in the space of the reference model to be enriched.

3. Computer non-transitory medium according to claim 2, in which the parent point is positioned in such a manner as to minimize said distance with the approximate surface and/or the approximate line.

4. Computer non-transitory medium according to claim 2, in which the approximate surface and/or the approximate line are determined by statistical methods or by means of a neural network.

5. Computer non-transitory medium according to claim 1, in which the first and/or second reference image is/are determined by means of a metaheuristic method.

6. Computer non-transitory medium according to claim 1, in which, in order to determine at least one of said first and second reference images, virtual acquisition conditions are sought in which the observation of the reference model to be enriched provides an image exhibiting a maximum match with said at least one of said first and second current images, respectively.

7. Computer non-transitory medium according to claim 6, in which said reference image is determined according to the following steps:
   a. processing of the current image in order to generate at least one current map representing, at least partially, a discriminating information;
   b. determination of virtual acquisition conditions to be tested;

c. generation of a reference image for the reference model under said virtual acquisition conditions to be tested, or "reference image to be tested";
d. processing of the reference image to be tested in order to form at least one reference map representing said discriminating information;
e. comparison of the current and reference maps in such a manner as to determine a value for a first evaluation function, said value for the first evaluation function depending on the differences between said current and reference maps;
f. depending on the value of the first evaluation function, modification of the virtual acquisition conditions to be tested, then return to the step c. or
definition of said reference image as being the reference image to be tested.

8. Computer non-transitory medium according to claim 7, in which the discriminating information is chosen from within the group consisting of contour information, color information, density information, distance information, brightness information, saturation information, information on the reflections and of the combinations of all these pieces of information.

9. Computer non-transitory medium according to claim 8, in which the discriminating information is contour information.

10. Computer non-transitory medium according to claim 1, in which the first and/or second reference image is/are sought by means of a metaheuristic method.

11. Computer non-transitory medium according to claim 1, the reference model to be enriched being generated by a scan of said arch of the patient.

12. Computer non-transitory medium according to claim 1, in which the reference model to be enriched is a current reference model obtained by deformation of an initial reference model of said arch, said method comprising the following steps:
1) at an initial time, generation of an initial reference model of said arch;
2) at a current moment in time, acquisition of said first and second current images;
3) deformation of the initial reference model in such a manner as to obtain said current reference model from which said first and second reference images exhibiting a maximum match with the first and second current images are observable.

13. Computer non-transitory medium according to claim 12, in which, at the step 3), the deformation of the initial reference model is determined by means of a metaheuristic method.

14. Computer non-transitory medium according to claim 1, comprising, after the step D), a step E) for comparison of the reference model to be enriched with the enriched reference model.

15. Computer non-transitory medium according to claim 14, in which, at the step E), a change in the shape and/or in the position of a tooth of the dental arch, and/or a loss of material resulting from an abrasion of said tooth are determined based on said comparison.

16. Computer non-transitory medium according to claim 1, in which the steps B) to D) are executed, in a loop, for more than 5 pairs of first and second current images.

17. Computer non-transitory medium according to claim 1, the first and second current images being acquired more than 2 weeks prior to the generation of the reference model to be enriched.

\* \* \* \* \*